United States Patent [19]
Lovoi

[11] Patent Number: 4,737,628
[45] Date of Patent: * Apr. 12, 1988

[54] METHOD AND SYSTEM FOR CONTROLLED AND SELECTIVE REMOVAL OF MATERIAL

[75] Inventor: Paul A. Lovoi, Saratoga, Calif.

[73] Assignee: International Technical Associates, Santa Clara, Calif.

[*] Notice: The portion of the term of this patent subsequent to May 13, 2003 has been disclaimed.

[21] Appl. No.: 862,285

[22] Filed: May 12, 1986

Related U.S. Application Data

[63] Continuation-in-part of Ser. No. 577,760, Feb. 7, 1984, Pat. No. 4,588,885.

[51] Int. Cl.$^4$ .............................................. G01N 21/27
[52] U.S. Cl. .............................. 250/226; 219/121 LB; 128/395; 250/205
[58] Field of Search ................................ 250/226, 205; 219/121 L, 121 LA, 121 LB, 121 LE, 121 LF, 121 LG, 121 LH; 128/395–398; 604/20–22

[56] References Cited

U.S. PATENT DOCUMENTS

| | | | |
|---|---|---|---|
| 3,700,850 | 10/1972 | Lumley et al. | 210/121 LB |
| 4,176,946 | 12/1979 | Takahashi | 250/226 |
| 4,381,894 | 5/1983 | Gogol, Jr. et al. | 356/72 |
| 4,588,885 | 5/1986 | Lovoi et al. | 250/226 |

*Primary Examiner*—Edward P. Westin
*Attorney, Agent, or Firm*—Thomas M. Freiburger

[57] ABSTRACT

A method and apparatus for controlling the removal of unwanted material from a site wherein there are present other materials utilizes pulses of high intensity radiant energy such as a laser beam. The control is accomplished by illuminating the site, with visible or invisible optical radiation, and subjecting the reflected optical radiation therefrom to spatial spectral dispersion. The spatial spectral dispersion is sensed and an electronic signal representative thereof is generated. The generated electronic signal is compared to a pre-recorded electronic signal representative of the spatial spectral dispersion of optical radiation reflected from the material to be removed before each pulse of high intensity radiant energy is applied to the surface, and the pulse is applied only upon such comparison resulting in a substantial match. Rastering with dithering is preferably used to accommodate industrial laser characteristics, to reduce site heating, to reduce the requirement of perpendicularity to the surface, and to accommodate contour features of the surface. Methods and means for normalization of the sensed spatial spectral dispersion and for utilizing mismatch comparisons are disclosed. The system is disclosed particularly in the context of surgical procedures for removal of tumors, bodies of matter causing blood vessel blockage, and other surgical procedures wherein selectivity between unwanted or deleterious material and normal tissue is critical.

17 Claims, 7 Drawing Sheets

METHOD AND SYSTEM FOR CONTROLLED AND SELECTIVE REMOVAL OF MATERIAL

REFERENCE TO RELATED APPLICATION

This application is a continuation-in-part of application Ser. No. 577,760, filed Feb. 7, 1984, now U.S. Pat. No. 4,588,885.

BACKGROUND OF THE INVENTION

This invention relates to the use of radiant energy for the controlled removal of a material or materials from a substrate or from a group of adjacent materials, controlled selectively without removing or damaging the substrate or the adjacent materials. The invention also emcompasses method and apparatus for the control of the removal process.

In copending application Ser. No. 577,760, filed Feb. 7, 1984, now U.S. Pat. No. 4,588,885, there is disclosed a system for the removal of paint and other coatings using high intensity radiant energy, e.g. a laser beam. An area of paint which is to be removed is subjected to spatial spectral dispersion from another beam of optical radiation, to identify the paint (or other coating) in that given area as material to be removed, or other material, not to be removed. The beam of optical radiation (e.g. visible light beam) is reflected off the material and the reflected beam analyzed, before the decision is made whether or not to direct the high intensity radiation on that area.

The entire disclosure of application Ser. No. 577,760, U.S. Pat. No. 4,588,885, is hereby incorporated by reference in this application, under the provisions of MPEP §608.01(p).

It is an object of the present invention to provide a method and system for controlled and selective removal of materials from sites where other materials are present, when said other materials are not to be removed. In particular, an important application is in surgical procedures. The invention uses the general principles disclosed in U.S. Pat. No. 4,558,885.

SUMMARY OF THE INVENTION

According to the method and apparatus of this invention, the removal of material from a surface or from among other materials includes impinging optical radiation having a given spectral range on a given area wherein material to be removed is present. The portion of the optical radiation which is reflected from the given area is subjected to spatial spectral dispersion. Such spatial spectral dispersion is electronically sensed and an electronic signal representative of such spatial spectral disperion is generated. A reference electronic signal representative of a given spatial spectral dispersion of optical radiation within the given spectral range is electronically compared with the reference electronic signal and if a substantial match is obtained, a high intensity beam of radiant energy (e.g. a laser beam) is impinged on such given area for a given period of time. The beam of radiant energy has a wavelength and power density sufficient to vaporize only a surface portion of the given area in the given period of time. The electronic signal generated after the impingement of the laser beam is again compared to the reference electronic signal and the alternate impingement of the laser beam and comparison of the generated electronic signal and reference electronic signal are repeated until the comparison results in a substantial mismatch at the end of a period of time during which the high intensity beam of radiant energy is impinged upon such given area.

In one specific application of the system of the invention, a laser beam is used to selectively remove unwanted tissue in a surgical procedure on the human body (or another living being). For example, a malignant tumor may be removed without damage to sensitive neighboring tissue, by recognition of the "color" or spectral characteristics of the tumor as opposed to the neighboring tissue. The selectivity of the invention enables successful laser surgery in difficult cases wherein the tumor tissue is actually intertwined with the subject's good tissue.

DESCRIPTION OF PREFERRED EMBODIMENTS

Many medical procedures require the removal of organic or foreign material from within or on the outside of a living organism. A wide range of techniques exist to carry out these procedures including chemicals, cutting, lasers, and ultrasound. This invention emcompasses a technique to control the removal process using an optical feedback signal.

Two basic criteria must be met for the process of the invention to succeed: The removal process must remove a small incremental layer of the desired material without eliminating the selection criteria, and the material to be removed must be distinguished from the surrounding and underlying material.

The process can be carried out directly in the open on exposed surfaces, either the surface of the body or areas exposed by surgery or within a body by means of fiber optics.

Figure 1:
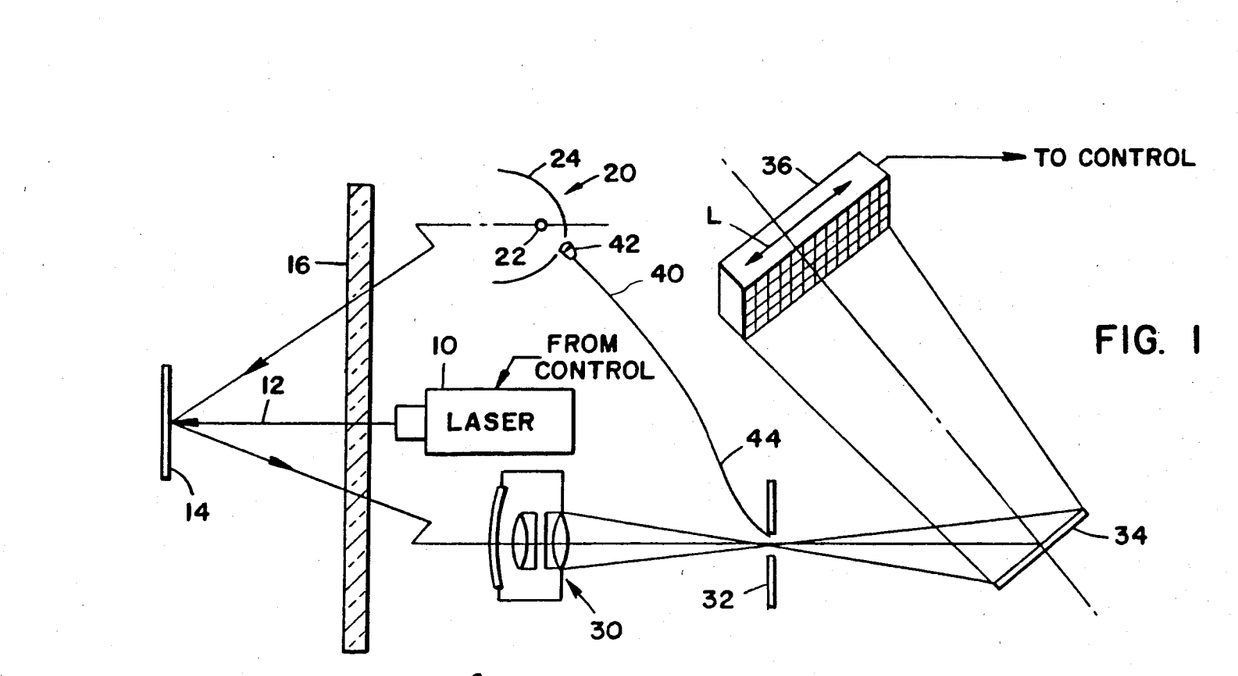
FIG. 1 is conceptual drawing showing the physical arrangement of the optically active elements of the method and apparatus of the invention.

Referring to FIG. 1 of the drawings, a laser 10 is shown with a beam 12 of radiant energy generated thereby impinging upon the surface 14 of a target. According to one embodiment of this invention, the surface 14 of the target or site is living tissue having bodies or components of deleterious matter to be surgically removed, such as tumors or other living or non-living matter in or on a human body or in or on an animal. The material to be removed may be intertwined with tissue of the subject which is to be saved.

Although the embodiments of this invention described hereinafter utilize a laser to generate the beam of radiant energy 12, it should be understood that other sources of high intensity radiant energy such as focused arc lamps, for example, could be used.

A transparent shield 16 of a material that will pass the beam 12 (or with a hole for passing the beam) may be interposed between the target 14 and the apparatus of the invention in order to protect the apparatus from the materials removed from the target by the action of the beam 12 of radiant energy. The shield generally is not necessary if fiber optics are used to conduct the beam 12 to the site 14 as discussed below.

For surgery the laser 10 may be of a type suitable for surgical procedures. For purposes of explanation only, the invention is illustrated with a $CO_2$ laser, which produces radiant energy having a 10.6 micron wavelength with high efficiency. A different type of laser may be optimum for laser surgery.

The laser 10 may have either a pulsed or a continuous output. Using pulsed output allows examination of the target before, between and after pulses for process control.

If the energy density and/or the pulse length is reduced, more pulses will be required to vaporize the full depth of a given layer of material but finer control of the process will be possible. If the energy density and/or the pulse length is increased, fewer pulses will tend to be required to remove the full depth of a given layer, but control of the process is more coarse.

The method and apparatus of the invention is based on the fact that the vaporization of increments of a layer of tissue or the like through the use of a high intensity beam of radiant energy will not substantially alter or discolor the remaining increments of the layer. This is believed to be due to the extremely high concentration of energy in the increment vaporized, the short time interval involved and the rapid dissipation of heat through vaporization, convection and conduction so that adjacent increments of the layer are not heated to a sufficient level to cause the alteration or discoloration thereof.

Thus, referring to FIG. 1, the basic optical elements of the method and apparatus of the invention are shown. For purposes of this discussion it will be assumed that the beam 12 of the laser 10 provides a footprint of one square millimeter having an energy density of five joules per square millimeter, although actual values selected for surgery may be quite different. In particular, the footprint may be smaller. It will further be assumed, again only for demonstration, that the laser 10 is capable of providing twenty microsecond pulses at a maximum pulse rate of about 1000 Hz.

According to the invention, the surface 14 of the target is illuminated by an appropriate source 20 of optical radiation which may be visible light or invisible optical radiation at either end of the spectrum.

The source 20 may be a quartz halogen lamp 22 provided with an appropriate reflector 24. The reflector 24 need not focus the light from the lamp 22 only on the one square millimeter footprint of the beam 12 but may flood the footprint together with a substantial surrounding area.

An objective lens system 30 focuses an image of the one square millimeter footprint area of the beam 12 on to the entrance aperture 32 of an imaging spectrometer comprising an anastigmatic flat field holographic grating 34 and a focal plane array detector 36. The anastigmatic flat field holographic grating 34 provides an image of the entrance aperture 32 on the focal plane arrey 36 such that position in the aperture 32 and wavelength will be truly orthogonal in the image on the focal plane array.

The spectral coverage of the system depends on the grating dispersion and focal length and on the length of the focal plane array.

It will be understood that as shown in FIG. 1, the light from the light source 20 which is reflected from the one square millimeter footprint area of the beam 12 will be focused by the lens system 30 through the aperture 32 onto the grating 34 which will provide a spatial spectral dispersion of such light along the length L of the focal plane array 36. Basically, the focal plane array comprises a plurality of individual silicon light sensor elements arranged in columns along the length L thereof. The image of the one square millimeter footprint area focused on the focal plane array may cover one or more columns of the silicon sensor elements. According to the embodiment shown in FIG. 1, the spatial spectral dispersion of the image of the one square millimeter footprint area is distributed over three columns along the L of the focal plane array ranging from the longer wavelenths at one of the length L of the array to the shorter wavelengths at the other end of the length L of the array 36.

The focal plane array 36 is a self-scanning device in which the silicon sensor elements of each column are scanned from one end to the other to produce an electronic signal in which time is representative of wavelength, and electrical output at a given point in time is representative of the intensity of the light at a particular wavelength. Thus the electronic signal output of the focal plane array may be coupled to an appropriate control device which is preferably a microprocessor having memory capability as more fully described hereinafter and in U.S. Pat. No. 4,588,885.

The basic operation of the method and apparatus is as follows with reference to FIG. 1. Light from the light source 20 impinges upon the surface 14 of the target or site including at least the area to be impinged by the footprint of the beam 12 of the laser 10. With the laser 10 turned off, the lens system 30 will focus an image of the footprint area through the aperture 32 onto the grating 34. The grating 34 will produce an electronic signal representative of the spatial spectral dispersion of light thereon which spatial spectral dispersion will be characteristic of the color of the tissue or other material on the surface 14 at the site. Such electronic signal will be recorded in the memory of the control unit and the laser 10 will be actuated to produce a pulse of radiant energy in a beam 12 impinging upon the footprint area. At the end of the laser pulse the silicon elements of the focal plane array 36 will again be scanned to generate a new electronic signal which will be coupled to the control unit for comparison to the electronic signal previously recorded in the memory thereof. If the comparison results in a substantial match between the previously recorded electronic signal and the newly generated electronic signal the laser 10 will again be actuated to produce a pulse of radiant energy. The above process is repeated until some substantial mismatch is found between the newly generated electronic signal and the electronic signal originally stored in the memory of the control device. When such a mismatch occurs, further laser actuation will be discontinued.

In order to avoid spurious readings and signals which may result due to changes in the spectral content of ambient light impinging upon surface 14 of the target, a fiber optic system 40 is preferably connected between the light source 20 and the aperture 32. Thus, a lens 42 couples light from the lamp 22 to a fiber optic cable 44. The fiber optic cable extends to a point immediately adjacent to the aperture 32. Thus, light from the lamp 22 is transmitted through the fiber optic system 40 and impinges upon the grating 34 immediately adjacent to the image of the footprint area. The grating 34 produces a spatial spectral dispersion of the light from the fiber optic system 44 on the focal plane array using array positions adjacent to those used for the footprint area to generate an electronic signal representative of the spectral content of the light from the lamp 22. Such electronic signal may be coupled to the control system and used for normalization of the electronic signals representative of the image of the footprint area. Thus any spectral content of the image of the footprint area introduced by ambient light can be subtracted during the comparison process.

Since the comparison can be made in about one millisecond, the pulse rate of the laser 10 may approach 1000 Hz. Due to the usual nature of industrial laser beams, the substrate of the target beneath the footprint of the beam 12 on the surface 14 will tend to be vaporized more deeply in the center than the edges of the footprint on each pulse. It is for this reason that vastering with dithering (i.e. shifting the entire raster pattern from pass to pass) is used for applying the beam 12. The resolution of the focal plane array is finer than the footprint area so that differences in the spatial spectral dispersion across the footprint may be detected in order to increase the sensitivity of detection of mismatch resulting in a more accurate application of the beam 12. It will be understood that if the spatial spectral dispersion detected at any one of the three columns fails to match the prerecorded spatial spectral dispersion, the laser 10 will not be actuated.

As mentioned hereinabove, overheating of the substrate may be avoided by moving the beam 12 through a raster.

Figure 2:
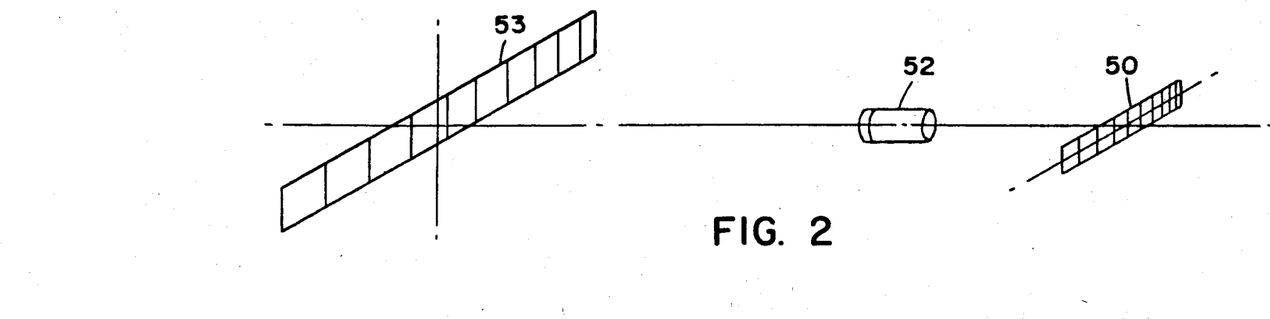
FIG. 2 is a conceptual drawing of one optically active element of the invention.

FIG. 2 shows a preferred modification of the apparatus of FIG. 1 to adapt it for use of a thirty-two by thirty-two element focal plane array in accommodating the rastering of the laser beam. Thus as shown in FIG. 2 the aperture 32 is modified to take the form of an elongated slit 50. A lens system 52 is provided to focus an image of an area 53 of the surface 14 of the target, which is ten millimeters long by one millimeter wide, on the slit 50. The focal adjustments of the apparatus are such that the entire image of the area 53 is focused on the grating with the light from each square millimeter unit of the area 53 being dispersed over three adjacent columns of the sensors of the focal plane array. Thus the focal plane array is capable of producing thirty independent electronic signals, three for each square centimeter of the image area 53.

Figure 3:
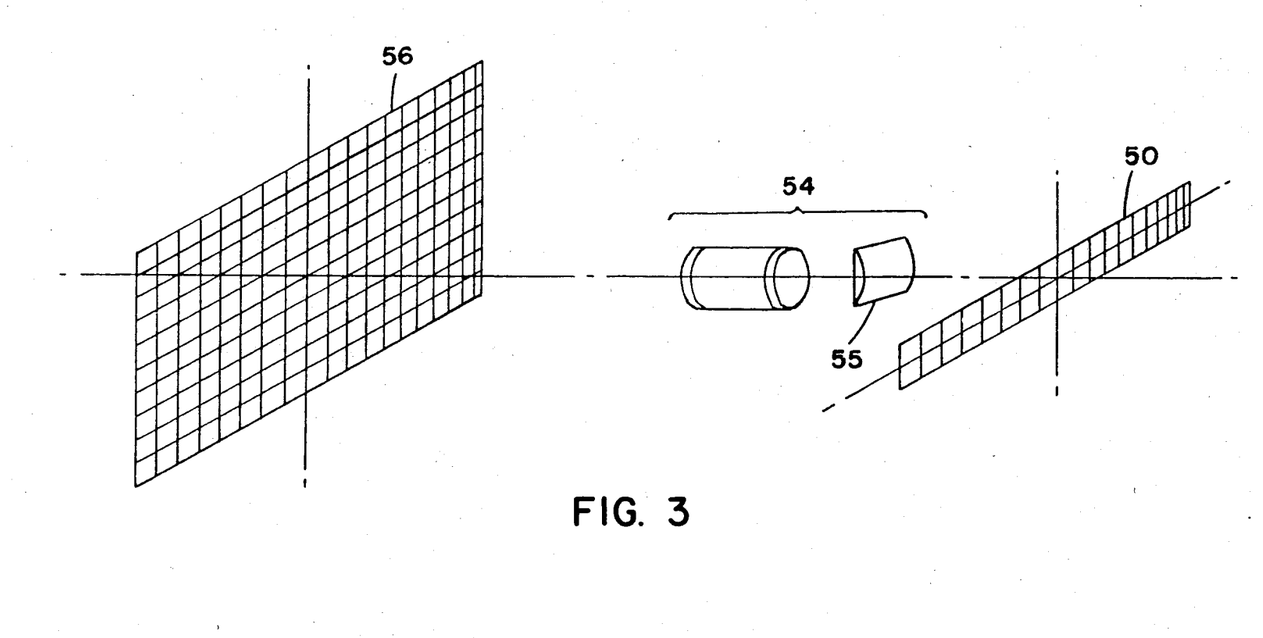
FIG. 3 is a conceptual drawing of a modification of FIG. 2.

FIG. 3 is discussed in the above-referred U.S. Pat. No. 4,588,885.

Figure 4:
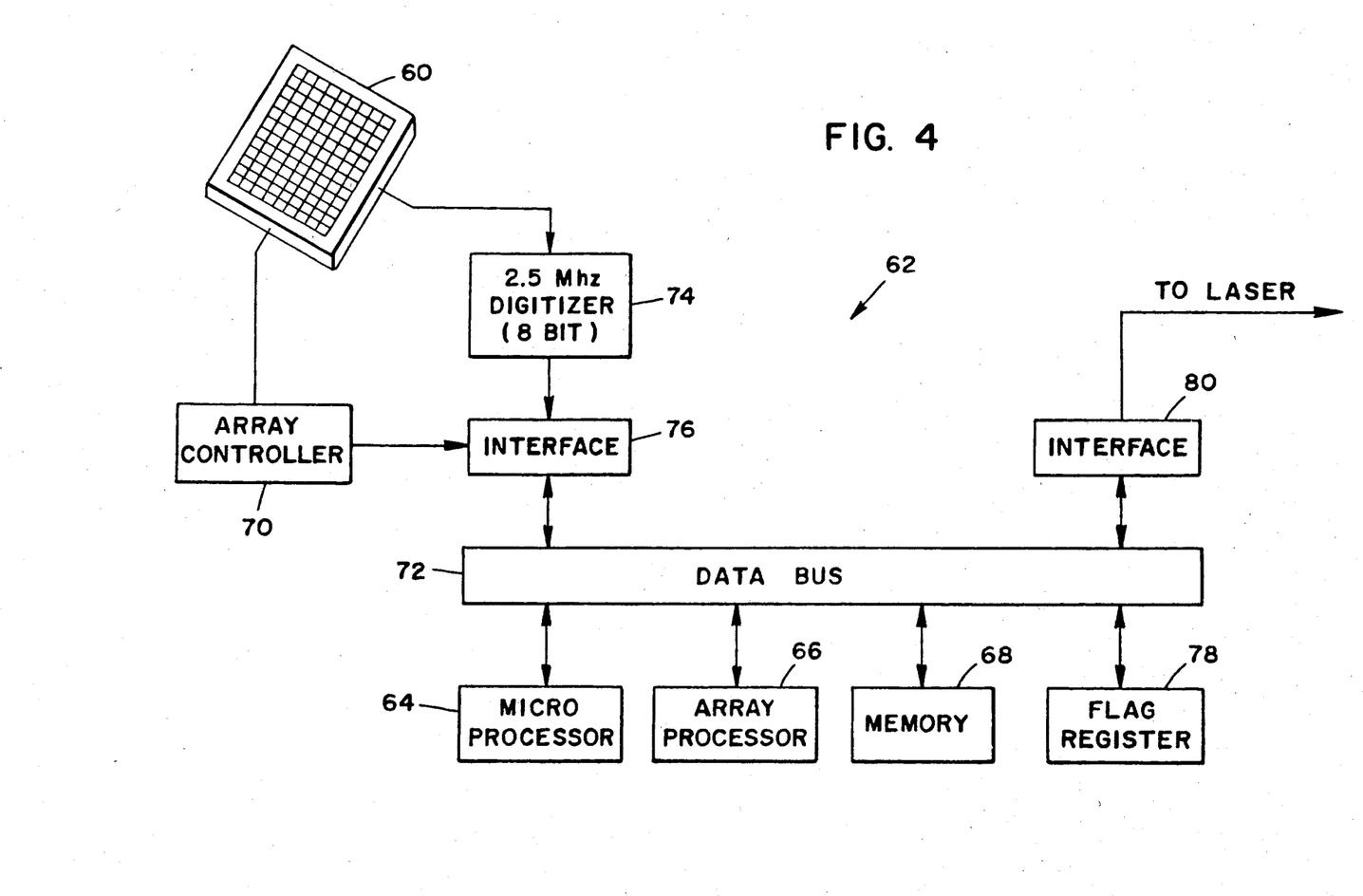
FIG. 4 is a general block diagram of the electronic elements according to a preferred embodiment of the invention.

Referring to FIG. 4, a thirty-two by thirty-two element focal plane array is represented at 60. It will be understood that the focal plane array 60 is physically mounted for movement together with the grating 34, slit 50, lens sysem 30, light source 20, laser beam 12 and shield 16. As such, the system is readily adaptable to robotics.

As will be described more fully hereinafter according to this emodiment of the apparatus of FIG. 1 modified as shown in FIG. 2, the beam 12 of the laser will be deflected to cover the area 53 in a raster. Thus the one square centimeter footprint of the beam 12 will be sequentially pulsed from left to right, for example, over the area 53 with each footprint impinging on a successive area. Other scanning sequences could be operated continuously during a continuous raster over the area 53. Thus the laser 10 will include an appropriate mirror system or other means for deflecting the beam 12 to cover the area 53 in one square millimeter increments.

Referring again to FIG. 4, the focal plane array 60 as well as the laser are connected by means of electrical/electronic cables to a controller 62 which may be at a remote location. Additional details of the controller 62 not discussed herein are disclosed in U.S. Pat. No. 4,588,885.

The controller 62 takes the electronic signals generated by each column of the focal plane array and determines whether the laser should be actuated for each one square millimeter unit of the area 53 of the surface 14 of the target. To this end, the controller 62 includes an array processor controller 70 which causes the electronic signal generated by each column of the focal plane array 60 to be coupled to the data bus 72 of the controller 62 through a 2.5 MHz eight-bit digitizer 74 and an appropriate interface 76. The microprocessor 64 and array processor 66 are programmed to compare the signals generated by each column of the focal plane array with the reference signals stored in the memory 68. The result of such comparison with each group of three adjacent columns of the focal plane array is recorded by a flag register 78.

The status of the flag register 78 is communicated to the laser 10 through an appropriate interface 80 to control each raster of the footprint of the laser beam over the area 53. Thus there are ten flags, one for each one square millimeter beam footprint unit of the area 53. The logic used by the controller is based on the requirement of recognition of the material to be removed. Thus the material must be recognized by a matching comparison of electronic signals before a flag is set to actuate the laser for the unit area involved. If at any time during the process the material is not recognized, the flag is not set and the laser will not be actuated for that particular unit area.

In operation, a given area 53 will be analyzed by the controller 62 as described hereinabove to set the flag register. While the laser is scannning the area 53, the controller 62 may be scanning an adjacent area 53 to re-set the flag register for that area.

Figure 5:
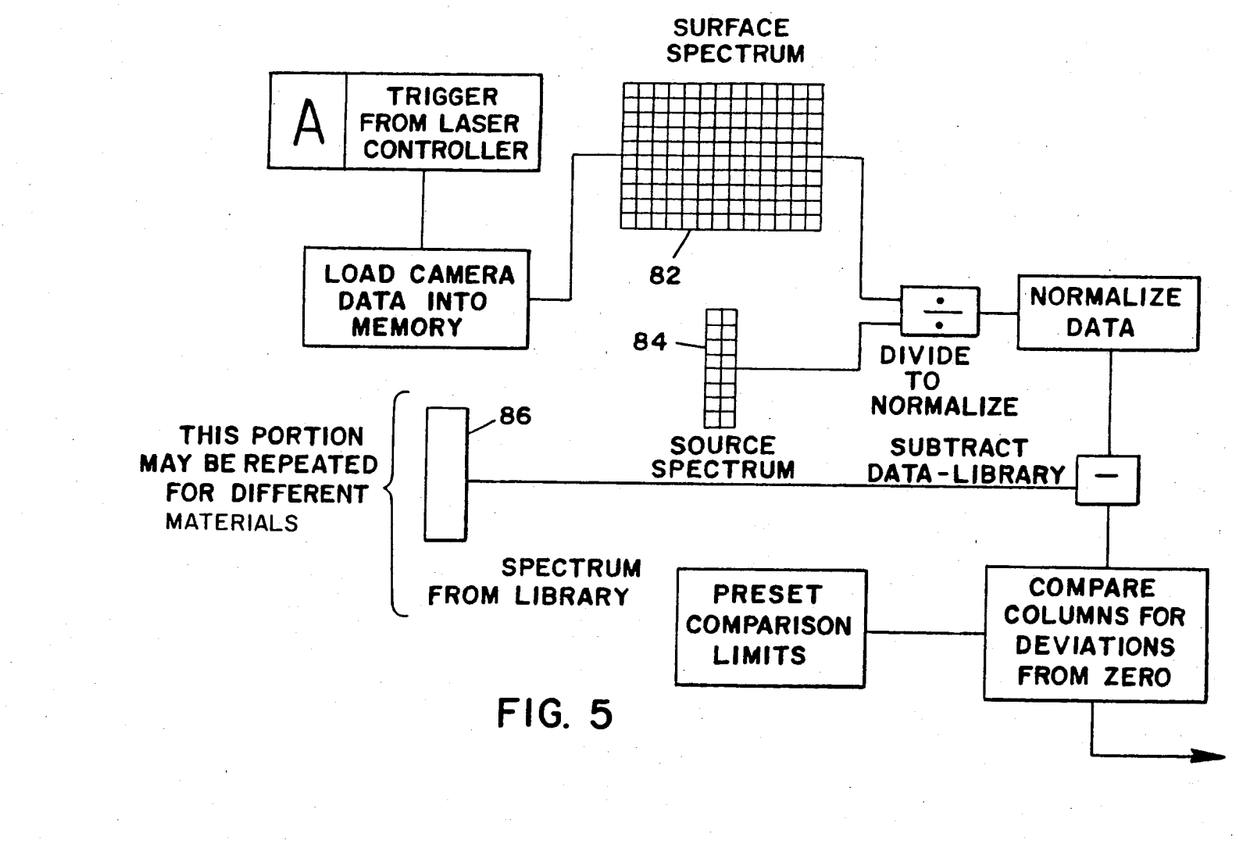
FIG. 5 is a detailed block diagram of a portion of FIG. 4.
Figure 6:
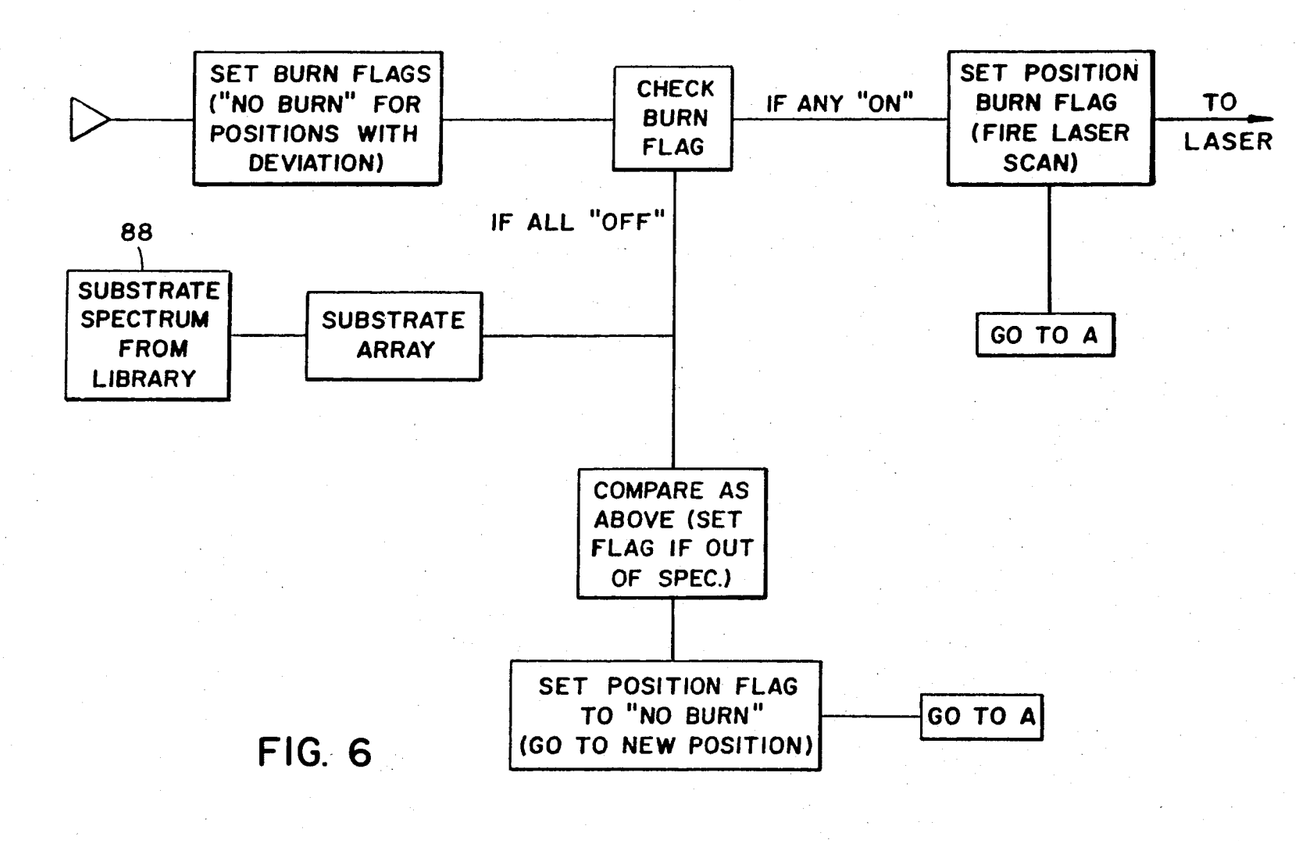
FIG. 6 is a detailed block diagram of the remainder of FIG. 4.

FIGS. 5 and 6 show further operational features of the invention and are discussed in U.S. Pat. No. 4,588,885.

It will be understood that each area 53 will be repeatedly scanned in whole or in part according to a raster pattern established by the microprocessor which will control the position of the laser beam 12 at the beginning of each scan. Such scanning will be repeated until every area 53 of the raster scan pattern fails to result in a burn flag.

Figure 7:
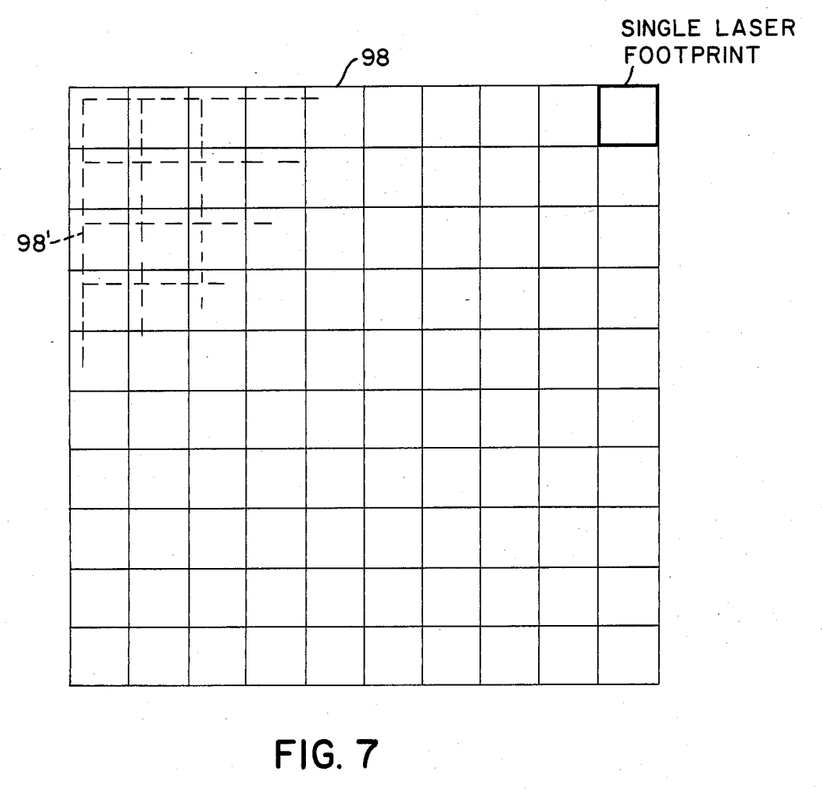
FIG. 7 is a diagrammatic view illustrating a scan pattern used with the invention.
Figure 8:
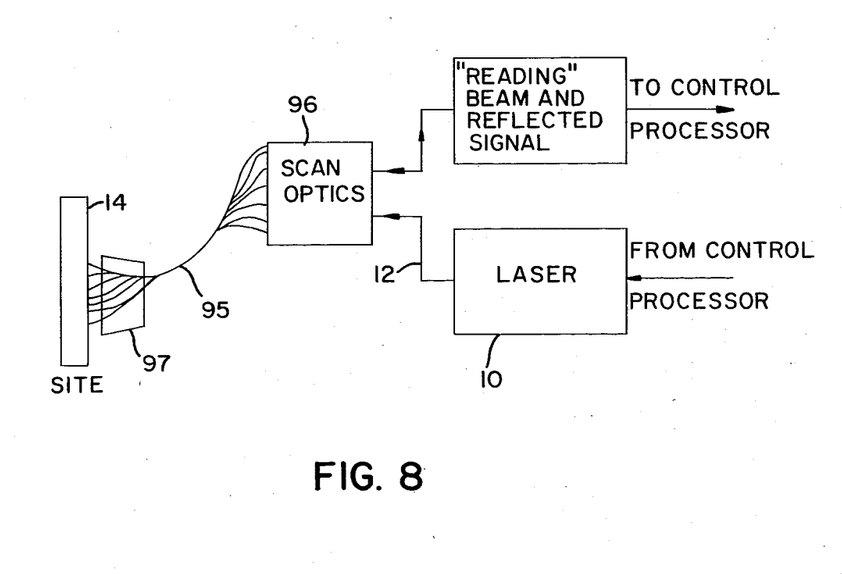
FIG. 8 is a schematic view to indicate the use of fiber optics in laser surgery in accordance with the invention.

The preferred embodiment of the invention for laser surgery uses a laser transmitted by a fiber optic bundle 95 as illustrated schematically in FIG. 8. The laser beam is scanned either by moving optics or solid state scanning by scanning optics 96 on the input end of the fiber optics. An image of the area to be removed is viewed, also through the fiber, by a vision system that can detect the "color" of each of several spatially resolved areas, in the same manner as discussed above. The surface 14 to be scanned is also illuminated by the fiber optic bundle. FIG. 8 shows that the "reading" beam of optical radiation and the reflected beam signed are passed through the scanning optics 96, with the reflected signal then passed to control processing. A probe tip is schematically indicated at 97. Typically a 32 color spectra of 30 spatial locations can be used. The pattern 98 to be scanned can be as represented in FIG. 7, for example. FIG 7 indicates that the rastering is with dithering. A second pass pattern position 98 is shown in FIG. 7.

The spectral camera preferably looks at a row at a time and compares, for example, three locations within each footprint to a library of stored spectra. This gives a total of 30 spectral elements across each row. When a footprint shows all of its locatings to be of a color that is to be removed, then that location is flagged for laser removal when the laser scan is correctly positioned.

Locations that do not have the right colors are flagged for no removal. After each pass over the pattern, the pattern is shifted slightly to insure smoothing of the edges of the removed area and to allow finer control of the removal process. The rastering technique allows less heating of the tissue because the energy is distributed over a larger area, providing a lower power density.

The spectral camera resolves the "color" into 32 separate wavelengths. These may cover the UV, visible or IR portion of the spectrum. The spectral range to be used depends on the materials being worked on and the contrast between them, assuring that all materials will be within the scan. The spectral signature is then electronically compared to a stored library of signatures and is either identified as a "to be removed" material or "anything else". This approach insures that only desired material is removed because it is positively identified.

Some materials change their signature as the outer material is removed. This can be accommodated by including both the top surface signature and the underlying material signature in the library.

Some examples of where such a removal process might be used are:

Clearing of arteries by removing an obstruction down to the artery wall without danger of damage to the wall.

Removal of a tumor on a sensitive underlying structure such as a gland or nerve without damage to the structure.

Removal of the exterior portion of a herniated disc without damage to the disc or remaining cartilage.

Removal of skin growths with high accuracy with minimum input power covering just the area to be removed.

The feedback control system can be implemented to allow only a selection function, not a control function. In this way a surgeon can provide the probe direction and laser fire selection and the control system can verify that the preset selection conditions desired by the surgeon have been met before firing the laser.

It is believed that those skilled in the art may make obvious modifications in the method and apparatus of the invention as described hereinabove without departing from the scope of the following claims.

What is claimed is:

1. A method of removing unwanted material selectively from a subject area or substrate where other materials not to be removed are present, comprising the steps of:

(a) impinging optical radiation having a given spectral range on a given area of the surface of the subject area;

(b) subjecting reflected optical radiation from the given area to spatial spectral dispersion;

(c) electronically sensing the spatial spectral dispersion and generating an electronic signal representative of the spatial spectral dispersion;

(d) electronically storing a reference electronic signal representative of a given spatial spectral dispersion of optical radiation within said given spectral range;

(e) electronically comparing the electronic signal with the reference electronic signal and upon the comparison resulting in a substantial match between the electronic signal and the reference electronic signal, impinging a high intensity beam of radiant energy on said given area of the surface of the subject area for a given period of time the beam of radiant energy having a wavelength and energy density sufficient to vaporize only a surface portion of the given area in said given period of time;

(f) after the given period of time, again electronically comparing the electronic signal with the reference electronic signal and again impinging the beam of radiant energy on the given area for said given period of time only upon the electronic comparison resulting in a substantial match between the electronic signal and the reference electronic signal, and (g) repeating step f) until the electronic comparison results in a substantial mismatch between the electronic signal and the reference electronic signal.

2. The method of claim 1, including the steps of: subjecting a portion of the impinging optical radiation having said given spectral range to spatial spectral dispersion, electronically sensing the spatial spectral dispersion and generating an electronic signal representative of the spatial spectral dispersion of said impinging optical radiation having said given spectral range; and utilizing the electronic signal representative of said spatial spectral dispersion of the impinging optical radiation having said given spectral range to normalize the electronic signal prior to comparing the electronic signal with the reference electronic signal.

3. The method of claim 1, including the steps of: electronically storing a further reference electronic signal representative of a spatial spectral dispersion different from the given spatial spectral dispersion; upon the electronic comparison resulting in a substantial mismatch between the electronic signal and the reference electronic signal, further electronically comparing the electronic signal and said further reference electronic signal; and upon said further electronic comparison resulting in a substantial match, again impinging the beam of radiant energy on said given area for said given period of time.

4. The method of claim 3, including the step of actuating a signalling means upon said further electronic comparison resulting in a substantial mismatch.

5. The method of claim 3, including the steps of: electronically storing yet another reference electronic signal representative of a spatial spectral dispersion which is not the same as said given spatial spectral dispersion and said different spatial spectral dispersion; upon said further electronic comparison resulting in a substantial mismatch, still further electronically comparing said electronic signal to said yet another electronic signal; and upon said still further electronic comparison resulting in a substantial mismatch, actuating a signalling means.

6. The method of claim 3, wherein the subject area is tissue of a living organism, the unwanted material being a body of deleterious material to be surgically removed.

7. The method of claim 1, wherein the subject area is tissue of a human body, the unwanted material being a body of deleterious material to be surgically removed.

8. The method of claim 7, wherein the high intensity beam of radiant energy is directed to the given area through fiber optics.

9. The method of claim 8, wherein the optical radiation and reflected optical radiation are directed to and from the given area through fiber optics.

10. The method of claim 1, wherein the opical radiation and reflected optical radiation are directed to and from the given area through fiber optics.

11. Apparatus for removing unwanted material selectively from a site where other materials, not to be removed, are present, comprising:
    (a) means for impinging optical radiation having a given spectral range on a given area of the surface of the site;
    (b) means for subjecting reflected optical radiation from the given area to spatial spectral dispersion;
    (c) means for electronically sensing the spatial spectral dispersion and generating an electronic signal representative of the spatial spectral dispersion;
    (d) means for electronically storing a reference electronic signal representative of a given spatial spectral dispersion of optical radiation within said given spectral range;
    (e) means for impinging a high intensity beam of radiant energy on the given area for a given period of time, said beam having a wavelength and energy density sufficient to vaporize only a surface portion of the given area in said given period of time;
    (f) means for electronically comparing the electronic signal with the reference electronic signal and actuating said means for impinging the beam on the given area for said given period of time only upon the electronic comparison resulting in a substantial match between the electronic signal and the reference electronic signal; and
    (g) means for actuating the means for electronically comparing the electronic signal with the reference signal both before and after each given period of time during which the means for impinging the beam is actuated.

12. The apparatus of claim 11, including
means for extracting an optical radiation sample from said means for impinging optical radiation;
means for subjecting said optical radiation sample to spatial spectral dispersion;
means for electronically sensing the spatial spectral dispersion and generating an electronic signal representative of the spatial spectral dispersion of the optical radiation sample; and
means for utilizing the electronic signal representative of said spatial spectral dispersion of the optical radiation sample to normalize the electronic signal prior to comparing the electronic signal with said reference electronic signal.

13. The apparatus of claim 11, wherein said means for subjecting the reflected optical radiation from said given area to spatial spectral dispersion comprises a lens means imaging the given area through an aperture onto an anastigmatic flat field holographic grating.

14. The apparatus of claim 13, wherein said means for electronically sensing said spatial spectral dispersion and generating an electronic signal representative thereof comprises a planar array of a plurality of silicon sensing elements located at the focal plane of the anastigmatic flat field holographic grating.

15. the apparatus of claim 11, wherein the means for impinging the high intensity beam includes fiber optics for directing the high intensity beam to the site.

16. The apparatus of claim 15, wherein the means for impinging and subjecting optical radiation include fiber optics for directing the impinging and reflecting optical radiation to and from the site.

17. A method for selective surgical removal of unwanted deleterious matter from normal tissue in or on the human body using a laser, comprising:
    directing a beam of optical radiation having a given spectral range onto a selected area of a site wherein the deleterious matter and the normal tissue are present,
    subjecting optical radiation reflected from the selected area to spatial spectral dispersion,
    electrically sensing the spectral dispersion and generating an electronic signal representative of the spectral dispersion,
    storing a reference electronic signal representative of a given spatial spectral dispersion of optical radiation within said given spectral range,
    electronically comparing the electronic signal with the reference electronic signal and, upon the comparison resulting in a substantial match between the electronic signal and the reference electronic signal, impinging a laser beam on the selected area for a given period of time, the laser beam having a wavelength and energy density sufficient to vaporize only a surface portion of the selected area in said given period of time;
    after the given period of time, again electronically comparing the electronic signal with the reference electronic signal and again impinging the laser beam on the selected area for said given period of time only upon the electronic comparison resulting in a substantial match between the electronic signal and the reference electronic signal, and
    repeating the previous step until the electronic comparison results in a substantial mismatch between the electronic signal and the reference electronic signal.

* * * * *

UNITED STATES PATENT AND TRADEMARK OFFICE
Certificate

Patent No.: 4,737,628

Patented: April 12, 1988

On motion pursuant to 37 CFR 1.634 in Interference No. 102,489, it has been found that the above-identified patent, through error and without any deceptive intention, incorrectly sets forth the inventorship. Accordingly, pursuant to 35 U.S.C. 256 it is hereby certified that the correct inventorship of this patent is: Paul A. Loyoi and Alan M. Frank.

Signed and Sealed this Nineteenth Day of November 1991.

STANLEY M. URYNOWICZ, JR.

*Examiner-in-Chief*
*Board of Patent Appeals*
*and Interferences*